(12) United States Patent
Zourob et al.

(10) Patent No.: US 7,492,978 B2
(45) Date of Patent: Feb. 17, 2009

(54) WAVEGUIDE STRUCTURE

(75) Inventors: Mohammed Zourob, Manchester (GB); Stephan Mohr, Manchester (GB); Bernard James Treves Brown, Manchester (GB); Peter Robert Fielden, Manchester (GB); Nicholas John Goddard, Manchester (GB)

(73) Assignee: The Secretary of State for Defence (GB)

( * ) Notice: Subject to any disclaimer, the term of this patent is extended or adjusted under 35 U.S.C. 154(b) by 120 days.

(21) Appl. No.: 10/529,970

(22) PCT Filed: Oct. 7, 2002

(86) PCT No.: PCT/GB02/04545

§ 371 (c)(1),
(2), (4) Date: Oct. 31, 2005

(87) PCT Pub. No.: WO2004/031743

PCT Pub. Date: Apr. 15, 2004

(65) Prior Publication Data

US 2006/0147147 A1    Jul. 6, 2006

(51) Int. Cl.
*G02B 6/00* (2006.01)
*G02B 6/26* (2006.01)

(52) U.S. Cl. .................. 385/12; 385/141; 385/143; 385/145

(58) Field of Classification Search .............. 385/12, 385/13

See application file for complete search history.

(56) References Cited

U.S. PATENT DOCUMENTS

| | | | |
|---|---|---|---|
| 4,649,280 A * | 3/1987 | Holland et al. ........... 250/483.1 |
| 4,818,710 A | 4/1989 | Sutherland et al. |
| 5,210,404 A * | 5/1993 | Cush et al. .................. 250/216 |
| 5,327,225 A | 7/1994 | Bender et al. |
| 5,344,784 A * | 9/1994 | Attridge ..................... 436/518 |
| 5,478,755 A * | 12/1995 | Attridge et al. ............. 436/518 |
| 5,843,651 A | 12/1998 | Stimpson et al. |
| 6,188,812 B1 | 2/2001 | Kao et al. |
| 6,483,096 B1 * | 11/2002 | Kunz et al. ............. 250/214 R |
| 6,483,959 B1 * | 11/2002 | Singh et al. .................... 385/12 |

FOREIGN PATENT DOCUMENTS

| | | |
|---|---|---|
| WO | WO 99/44042 | 9/1999 |
| WO | WO 01/42768 | 6/2001 |

* cited by examiner

*Primary Examiner*—Michelle R Connelly Cushwa
(74) *Attorney, Agent, or Firm*—Dean W. Russell; Kilpatrick Stockton LLP

(57) ABSTRACT

A novel single point leaky waveguide structure and its use as an optical sensor for the detection of particles is disclosed. The waveguide structure is fabricated to increase the overlap of the evanescent field extension from the sensor surface with particles in the bulk solution of a flowing system so as to place most of the volume of the particles within the evanescent field. Increasing the overlap of the evanescent field with the particles and permitting mode propagation along the direction of flow for a few millimetres provides an effective interrogation approach for multiple particle detection in a single flow channel.

10 Claims, 10 Drawing Sheets

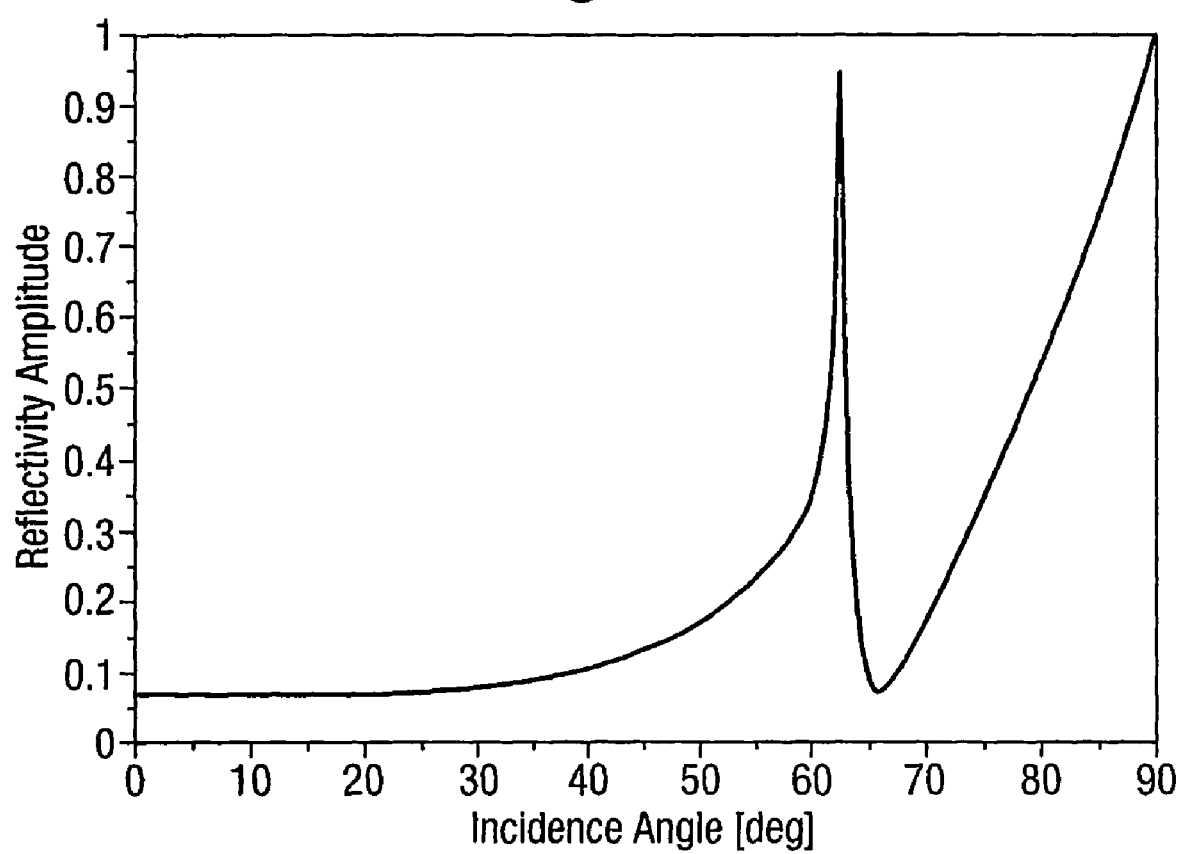

Figure 10C:
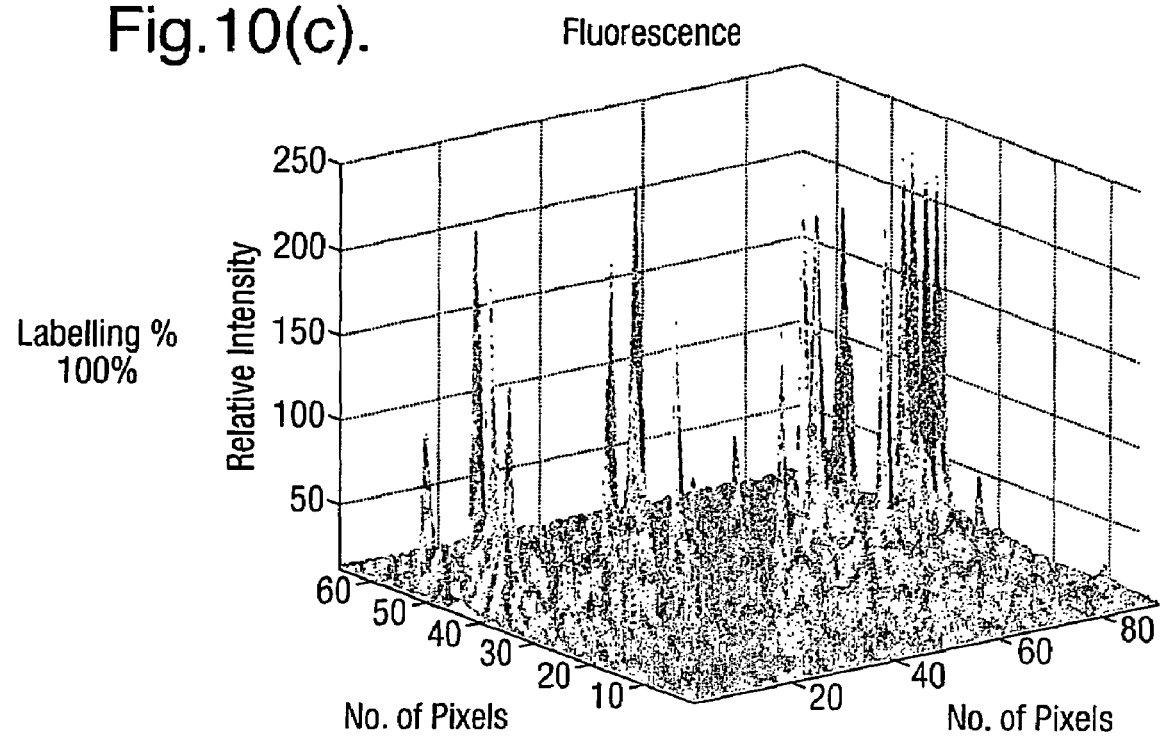
Figure 10D:
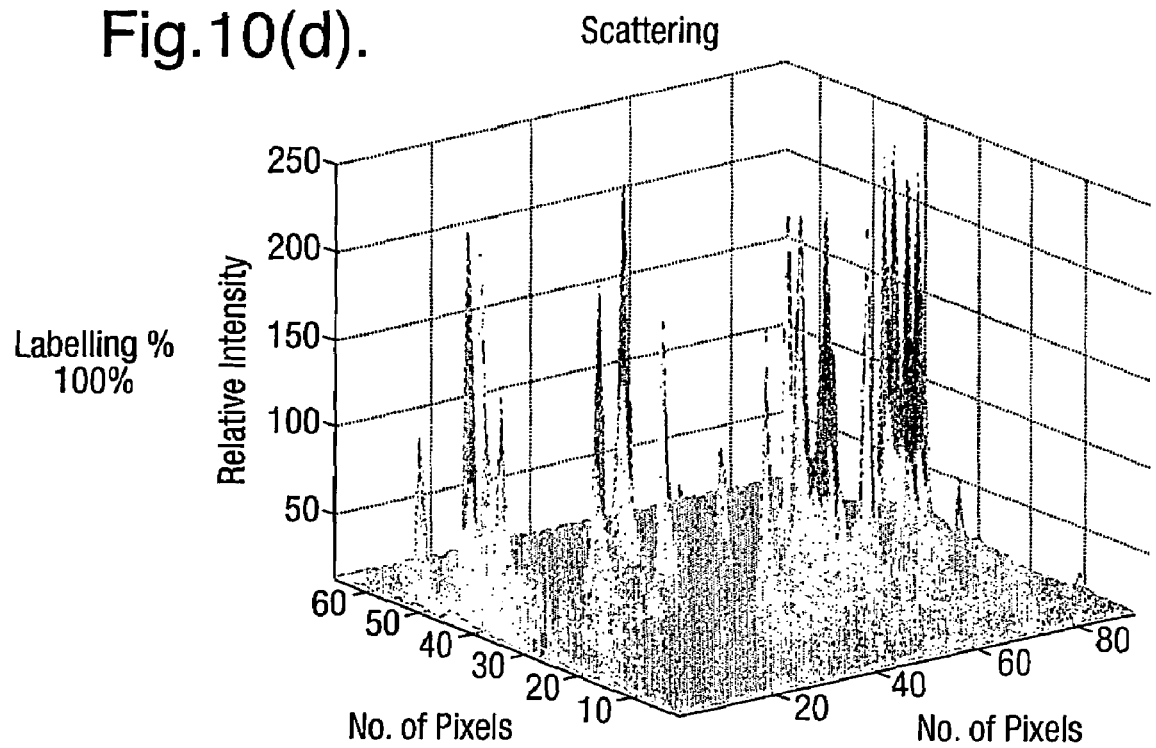

Fig.10(a). Fluorescence
Labelling % 10%
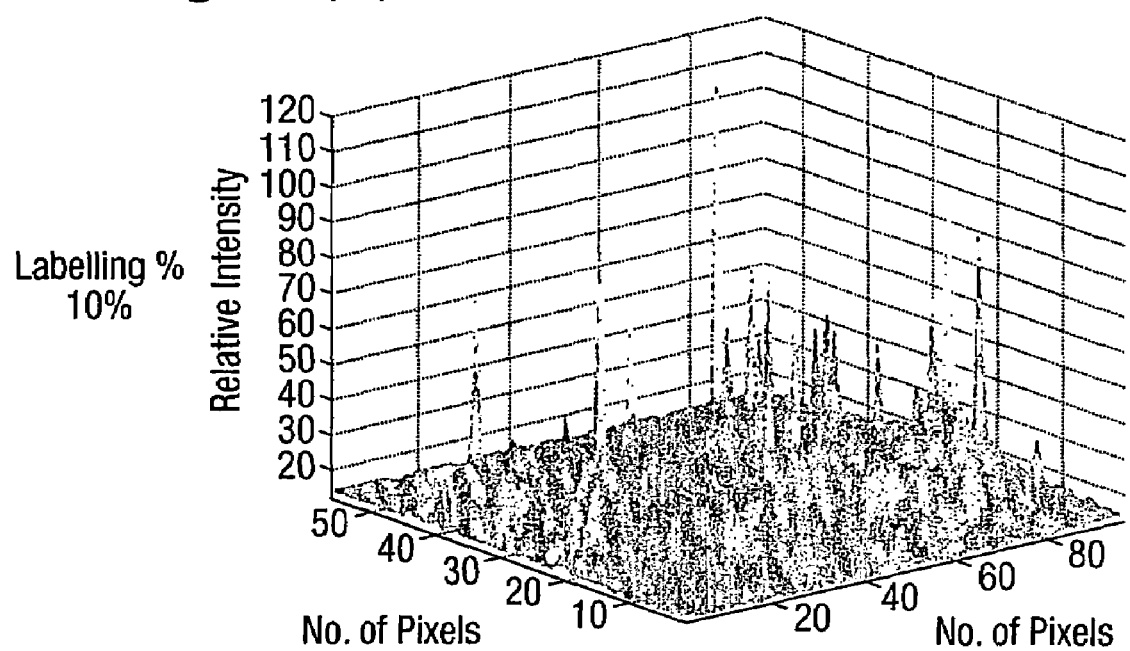
Fig.10(b). Scattering
Labelling % 10%
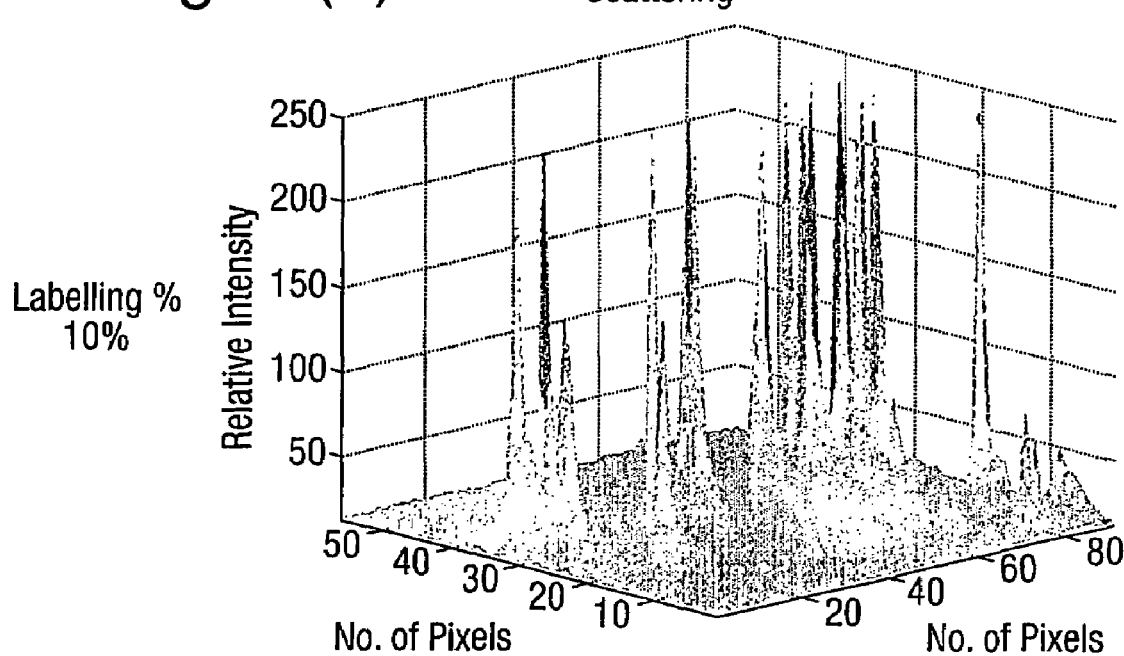

WAVEGUIDE STRUCTURE

CROSS REFERENCE TO RELATED APPLICATIONS

This application is the U.S. national phase of International Application No. PCT/GB2002/004545 filed on Oct. 7, 2002 and published in English on Apr. 15, 2004 as International Publication No. WO 2004/031743 A1, the contents of which are incorporated by reference herein.

The present invention relates to waveguide structures and is particularly, although not exclusively, directed to waveguide structures suitable for use as optical biosensors.

The recent increase in the prevalence of antibiotic-resistant bacteria and the escalated risk of biological warfare or terrorism have emphasised the need for a rapid and cost effective determination of the presence of pathogens in both the civilian and military environment. Optical sensors provide a superior method for the detection of pathogens in that they allow real-time monitoring of an environment according to changes in an optical property associated with a biological sample.

Optical sensors are commonly based on layered optical waveguide structures in which an evanescent wave associated with an optical mode existing in the structure extends into a sensing layer comprising the biological sample. A change in the refractive index, for example, of the sample by interaction or binding to the pathogen leads to a change in an optical property of the mode, which can be readily detected. Optical waveguide structures have been used to detect pathogens such as bacteria, viruses and toxins in water.

One such optical evanescent sensor uses the phenomenon of surface plasmon resonance (SPR). Here the sensor comprises a dielectric prism in which an upper surface is coated with a thin metal layer of gold or silver and a sensing layer comprising the biological sample is arranged on the metal layer. Light incident the upper surface of the dielectric prism at angles greater than the critical angle for total internal reflection is monitored by a detector. At a certain "resonant" angle or angles, the incident light is coupled to oscillations of the electron cloud in the metal layer and is propagated at the interface of the prism and the metal layer. A drop in the amount of reflected light is detected at the detector. The surface optical mode generates an evanescent field that extends into the sensing layer and is sensitive to a change in the refractive index of the biochemical sample. A pathogen binding to the sample is detected at the detector by a change in the angle at which resonance is excited.

The sensitivity of optical sensors based on surface plasmon resonance is in general restricted in that the range of angles at which the incident light will excite resonance is small. The problem is particularly acute for the detection of particles where the requirement for a relatively large change in the refractive index of the biochemical sample is compounded by poor extension of the evanescent field into the sensing layer. A further disadvantage of optical sensors based on surface plasmon resonance is that they require polarised light.

One approach to the problem of poor sensitivity, described in International Patent Application No. WO 99/44042, relies on optical sensors comprising "leaky" waveguide structures. The basic "leaky" waveguide structure is similar to the surface plasmon resonance structure in that it comprises a sensing layer disposed upon a thin metal layer coating a transparent substrate. However, the refractive indices of the layers are chosen so that light incident the upper surface of the substrate is not wholly internally reflected but coupled through the metal layer into (and out of) an optical mode propagating in the sensing layer.

WO 99/44042 describes a number of other leaky waveguide structures. One structure (a resonant optical waveguide, ROW) comprises a sensing layer provided on a layer of high refractive index, which is disposed upon a spacer layer separating it from the substrate. In this structure, which is similar to a resonant mirror structure, light incident the upper surface of the substrate is coupled via an evanescent field in the spacer layer into an optical mode supported in the layer of high refractive index. The optical mode has itself an associated evanescent field, which extends into the sensing layer. A further structure (an anti-resonant reflecting optical waveguide, ARROW) comprises an additional spacer layer between the layer of high refractive index and the sensing layer. The refractive indices and thicknesses of each layer are chosen so as to maximise the reflection of propagated light in the leaky waveguide mode by constructive interference and to minimise its loss by destructive interference.

It will be understood that because the leaky waveguide structures of WO 99/44042 support an optical mode centred on the bulk of the sensing layer (a "bulk" optical mode) they offer greater sensitivity than waveguides based supporting surface modes. A further advantage of the waveguide structures of WO 99/44042 is that they can provide an easily observed peak, rather than a dip, in the intensity of reflected light. for a large change in the refractive index of the sample.

Improved sensitivity of detection of particulate pathogens is obtainable by examination of light scattered or emitted by interaction of particles with an optical mode. International patent application No. WO 01/42768 describes the use of surface plasmon resonance to detect particles by scattering or emission of light. The sensitivity of the technique is limited by the fact that the extension of the evanescent field in the sensing layer is low (about 100 to 250 nm) and therefore overlaps only a small proportion of the bulk of particles such as bacteria (about 1 μm in diameter). Further, because the intensity of scattered or emitted light is proportional to the intensity of the evanescent field, which diminishes exponentially in the sensing layer, poor extension of the field means that particles further from the interface of the sensing layer with the metal may not be detected.

The leaky waveguide sensors of WO 99/44042 are also limited in their ability to detect pathogens by scattering of light. In particular, the pore sizes must be constrained in order to avoid them scattering light and thus can only admit particles of diameters less than 20 nm. Consequently larger particles such as bacteria and some viruses cannot be detected using this method.

The present invention generally aims to overcome these problems by providing a waveguide sensor in which an evanescent field penetrates a sensing layer to a greater extent and overlaps with at least a major proportion of the bulk of the particle. The present invention lies in the realisation that a leaky waveguide optical mode supported in a layer of low refractive index adjacent a sensing layer can increase the depth of penetration of an evanescent field in the sensing layer.

The present invention therefore provides a waveguide structure comprising a sensing layer of a medium disposed upon a second layer, said second layer being disposed upon a third layer of differing refractive index to the second layer, in which the structure is capable of supporting a bulk optical mode in the second layer, the medium is adapted to trap a target particle that results in a change in an optical property of the sensing layer and the thickness and/or refractive index of the second layer is selected to control the depth of penetration of the optical mode into the sensing layer and to overlap at least a major portion of the particle.

It will be understood by those skilled in the art that the selection of refractive index and thickness of the second layer modulates the refractive index of the third layer and improves the optical mode and the depth of penetration of its evanescent field in the sensing layer. In general, the extent of penetration of the evanescent field increases with diminishing thickness and lower refractive index of the second layer. Preferably, the refractive index of the second layer is lower than the refractive index of the third layer.

The second layer also acts to increase the extent of propagation of the evanescent field in the sensing layer. The propagation of the mode in the sensing layer can reach a few mm and is much higher than the few microns obtainable in surface plasmon resonance and resonant mirror waveguides. It will therefore be apparent that the second layer also increases the area of detection of a sensor based on the waveguide structure.

In a preferred embodiment of the present invention, the second layer comprises silica in crystalline or sol gel form. However, the second layer may alternatively comprise other materials capable of supporting an optical mode such as agarose gel, certain fluorinated polymers or polyacrylates such as poly-2-hydroxyethylmethylacrylate (Hydrogel™).

In a preferred embodiment of the present invention, the waveguide structure comprises a fourth, absorbing layer, of high reflectivity, disposed between the second layer and the third layer. The fourth layer may comprise a thin metal layer or coating provided on the upper surface of the third layer (in which case the structure is described as a "metal-clad" leaky waveguide, MCLW). Suitable metals include aluminium, tantalum, zirconium, titanium or chromium. Alternatively the fourth layer may comprise a thin layer or coating of a crystalline dye material (in which case the structure is described as a "dye-clad" leaky waveguide, DCLW).

The inclusion of a fourth layer, is advantageous in that it furthers propagation of the optical mode in the second layer and increases the depth of penetration of the evanescent wave in the sensing layer. The fourth layer therefore also improves the sensitivity of the waveguide structure. Further, when the waveguide mode is not excited, (i.e. it is in "off resonance" mode in which light is not coupled into the waveguide), almost all of the incident optical energy is deposited on the layer in the form of heat. Thus, at resonance, there is a sharp peak in the reflectivity of the MCLW or DCLW making detection of the resonant mode at a detector relatively easy.

Suitable refractive indices n for the second layer, resulting in improved detection of bacteria of size 1 to 10 µm, range from n 1.33 to 1.45 with suitable thicknesses for the second layer ranging from 200 nm to 1000 nm. Preferably, the refractive index and thickness of the second layer is chosen so that the depth of penetration of the evanescent field overlaps the whole of the particle to be detected.

In one embodiment of the present invention a second layer comprising silica sol of thickness 300 nm and a fourth layer comprising titanium of thickness 8.5 nm is suitable to give a depth of penetration of the evanescent field of at least 1.5 μm and full overlap *Bacillus globigii,* (BOG), spores (~1 μm).

The third, or "substrate" layer of the waveguide structure generally comprises a light transmitting material such as glass, Perspex®, quartz or a suitable polymer and may be associated with means for coupling light into and out of the second layer of the structure. Preferably, the substrate layer comprises an ordinary microscope slide.

The waveguide structure of the present invention may be fabricated as a "chip" which can be adapted by the end user. The chip may be provided by coating a conventional microscope slide with a thin metal or dye layer, followed by spin coating or vacuum deposition of the silica layer. Whilst the thickness of the metal or dye layer will be fixed at the time of manufacture, the present invention contemplates that the thickness of the silica layer or silica sol layer may be determined by subsequent treatment of the chip. In particular, the chip may be adapted for the detection of one or more particles by, for example, etching the whole or a portion of the silica layer to give a desired thickness. Of course, in these circumstances the chip will be manufactured to a thickness of the silica or silica sol layer suitable for the detection of the largest of particles of potential interest. The final thickness of the silica or silica sol layer is determined by the end user and the disposition of the sensing layer on the chip.

The sensing layer may comprise an antibody layer or coating, which is chemically deposited on the chip by standard reaction with chemical linking groups known to the art. The antibody layer or coating may be continuous or partial and may, in particular, comprise a number of continuous or partial arrays of different antibodies each specific to a different particle to be detected. In one embodiment of the present invention a *Bacillus globiggi* antibody layer or coating is attached by sequential exposure of the chip to 3-aminopropyltriethoxysilane, glutaraldehyde and antibody.

It will be realised that the sensing layer of the present invention may alternatively or additionally comprise a fluid layer in contact with the upper surface of the chip. The fluid layer, which is semi-infinite, will contain the particles to be detected. It will also be realised that chemical or biochemical entities other than antibodies, which are specific to a particle to be detected, may be used in the sensing layer.

In one aspect of the present invention there is provided an optical sensor comprising a waveguide structure having a sensing layer of a medium disposed upon a second layer, said second layer being disposed upon a third layer of differing refractive index to the second layer, in which the structure is capable of supporting a bulk optical mode in the second layer, the medium is adapted to trap a target particle resulting a change in an optical property of the sensing layer and the thickness and/or refractive index of the second layer is selected to control the depth of penetration of the optical mode in the sensing layer and to overlap at least a major portion of the target particle, an optical source, means for coupling light from the optical source to the optical mode and means for detecting light scattered or emitted by the particle in, at or adjacent the sensing layer.

The detecting means generally comprises a charge-coupled device (CCD) imager. The detecting means may be associated with an imaging lens disposed between the sensing layer and the imager. Preferably, the imaging lens comprises two achromatic lenses and in conjunction with the CCD imager gives a resolution of about 4 μm per pixel.

The detecting means is arranged above the upper surface of the chip to detect scattered or emitted light from the particle. The emitted light may be due to fluorescence although phosphorescence may also be used. Of course if emitted light is to be detected the particle must first be suitably labelled or otherwise be a natural emitter.

The wavelength of the incident light will be chosen not only to support emission of light by the particle but also to optimise the depth of penetration of the evanescent field in the sensing layer and provide a convenient angle of incidence of the light at the upper surface of the third layer.

The optical source generally comprises a source of coherent light. Where fluorescence is to be detected the optical source may comprise an argon laser providing light at 488 nm. A suitable filter removing scattered light is placed in front of the CCD imager. Where scattered light is to be detected, the filter may be exchanged for one removing any emitted light or an optical source comprising a semiconductor laser providing light at 635 nm wavelength may be used.

The optical sensor may further include means for detecting changes in the properties of the optical mode by monitoring light coupled from the waveguide structure. Although the peak of amplitude of reflected light at resonance is sharp, the second detector cannot detect individual particles in the way that the first detector can, and is provided solely for the purpose of maintaining the incident light at the appropriate resonant angle.

In a second aspect of the present invention there is provided a method of detecting a particle comprising the steps of i) exposing the optical sensor to the target particle and ii) detecting light scattered or emitted from the particle at the detecting means.

In a further aspect of the present invention provides for use of a waveguide structure comprising a sensing layer of a medium disposed upon a second layer, said second layer being disposed upon a third layer of differing refractive index to the second layer, in which the structure is capable of supporting a bulk optical mode in the second layer, the medium is adapted to trap a target particle that results in a change in an optical property of the sensing layer and the thickness and/or refractive index of the second layer is selected to control the depth of penetration of the optical mode into the sensing layer and to overlap at least a major portion of the particle, in a method of detecting the particle.

It will be apparent to those skilled in the art that the invention provides a technique based on the collection of scattered or emitted light which improves on surface plasmon resonance and resonant mirror techniques by increasing the probability and extent of overlap of the evanescent field with the particle. Indeed the invention makes possible detection of *Bacillus globiggi* at concentrations of $10^7$ spores ml$^{-1}$—an improvement of two orders of magnitude compared to the prior art (typically $10^9$ spores ml$^{-1}$). Other advantages of the present invention include the fact that unlike the surface plasmon resonance technique there is no need to use plane polarised light and that much lower angles of incidence are used. Further, the waveguide structures of some embodiments of the present invention can be fabricated at room temperature, are cheaper to manufacture and can be disposable.

The present invention will now be described with reference to a number of embodiments and the following drawings in which FIG. 1 is a diagram illustrating the generation of an evanescent field at the interface of media in which total internal reflection of light occurs;

FIG. 2 is a schematic representation of a “leaky” waveguide structure;

FIG. 3 is a cross sectional elevation view of a leaky waveguide structure according to one embodiment of the present invention;

FIG. 4 is a graph showing the optical mode supported in the waveguide structure according to the embodiment of FIG. 3;

FIG. 5 is a graph showing the relative extent of the evanescent field in the sensing layer for the embodiment of FIG. 2 and for SPR and resonant mirror waveguide structures;

FIG. 6 is a schematic illustration of an optical sensor according to the present invention;

FIG. 7 is a graph illustrating the peak in reflectivity of the optical sensor of FIG. 6;

FIGS. 8*a*) to *c*) show scattering of light before and during exposure of the chip to latex beads FIGS. 9*a*) and *b*) illustrate fluorescence and scattering of light during exposure of the chip to fluorescein labelled 5 μm latex beads for different optical sources;

FIGS. 10*a*) to *d*) illustrate fluorescence during exposure of the chip to 100% and 10% fluorescein labelled 5 μm latex beads;

FIGS. 11*a*) and *b*) illustrate fluorescence during exposure of the chip to yeast cells expressing the protein GFP; and FIG. 12 shows scattering of light from of BG spores captured an antibody coated chip.

Referring now to FIG. 1, wherever light 11 is incident an interface 12 of media of differing refractive indices $n_1$ and $n_2$ at an angle greater than a critical angle $\theta_c$ for total internal reflection within the optically denser medium, it generates an evanescent field 13, by conservation of momentum and energy. The evanescent field or wave 13 propagates in parallel to the interface 12 within the optically less dense medium with an intensity, represented as the curve, which can be expressed $$I_{ev}=I_o\,exp(-z/d_p)$$

where $I_o$ is the intensity of the evanescent wave at the point of reflection, z is the distance of the wave from the point of reflection, and $d_p$ is the depth of penetration of the wave in the optically less dense medium.

The depth of penetration of the wave $d_p$ is a function of the wavelength λ and angle $\theta_i$ of the incident light and governed by the relationship:

$$d_p = \frac{\lambda/n_1}{2\pi\sqrt{\sin^2\theta_i} - (n_2/n_1)^2}$$

Referring now to FIG. 2, a “leaky” waveguide structure is based on a similar arrangement in which the refractive indices $n_1$ and $n_2$ of the media are “matched” so that at a certain angle or angles $\theta_i$ not all the incident light is reflected. Total internal reflection is now “frustrated” and a proportion of the light is coupled, without generating an evanescent field, from the optically denser medium to the optically less dense medium.

Where the optically less dense medium is in contact with a further medium of lower refractive index $n_3$ the coupled light will be returned by total internal reflection at the interface 14 between the two media. It will be apparent therefore, that because only a proportion of light is coupled back to the optically denser medium, an optical mode 15 is propagated within the optically less dense medium. It will further be realised that the optical mode 15 includes an associated evanescent field 13, which propagates in the medium of lower refractive index.

The optical mode 15 and its associated evanescent field 13 are sensitive to changes in the refractive index of the medium of lower refractive index and can excite scattering or emission of light 16 by particles 17 in the vicinity. It will be apparent that, because the intensity of scattered or emitted light is dependent on the intensity of the evanescent field, the particle 17 is more strongly illuminated the greater the depth of penetration of the evanescent field 13.

Referring now to FIG. 3 a leaky waveguide structure according to the present invention comprises a chip, generally designated 18 comprising an upper surface of a 300 nm silica sol layer 19 (n=1.43) provided on a thin layer (8.5 nm) of titanium 20 coating a 1 mm glass substrate layer 21 (n=1.5). The thickness and refractive index of the silica sol layer 19 is chosen to support a single sharp-guided optical mode 15 at a wavelength of incident light of 685 nm or 488 nm and to optimise the depth of penetration (about 1.5-2.0 μm) of the evanescent field.

The sensing layer 22 can comprise a layer of a biochemical sample to be analysed. Alternatively or in addition, the sensing layer 22 can comprise an antibody layer deposited on the silica sol layer 19 of the chip 18 by soaking in 10% 3-aminopropyltriethoxysilane (APTS) for 4 h, washing with ethanol and drying at 110° C. for 2 h. The chip 18 is then activated for detection of Bacillus globigii by soaking with 5% aqueous glutaraldehyde for 30 min followed by exposure with suitable antibody solution of concentration 300 μg ml$^{-1}$ in 10 mM phosphate buffer (pH 7.4) for 30 min. Finally, unreacted sites on the chip 18 are blocked by exposure of the chip 18 within the flow cell to 5 mg ml$^{-1}$ aqueous bovine serum albumin (BSA).

Figure 4:
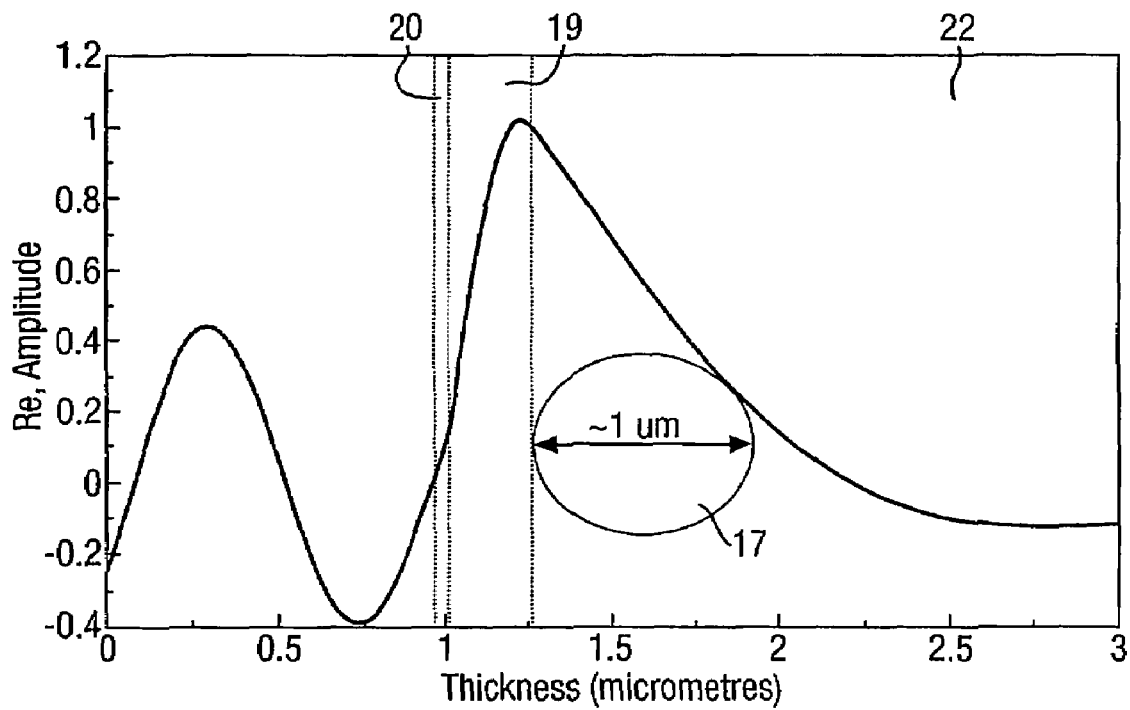

FIG. 4 shows the optical mode supported in the silica sol layer 19 of the chip 18 including its associated evanescent field 13. As may be seen, the mode 15 is a single sharp guided mode in which the depth of penetration of the evanescent field 13 extends to overlap a particle in the sensing layer 22.

Figure 5:
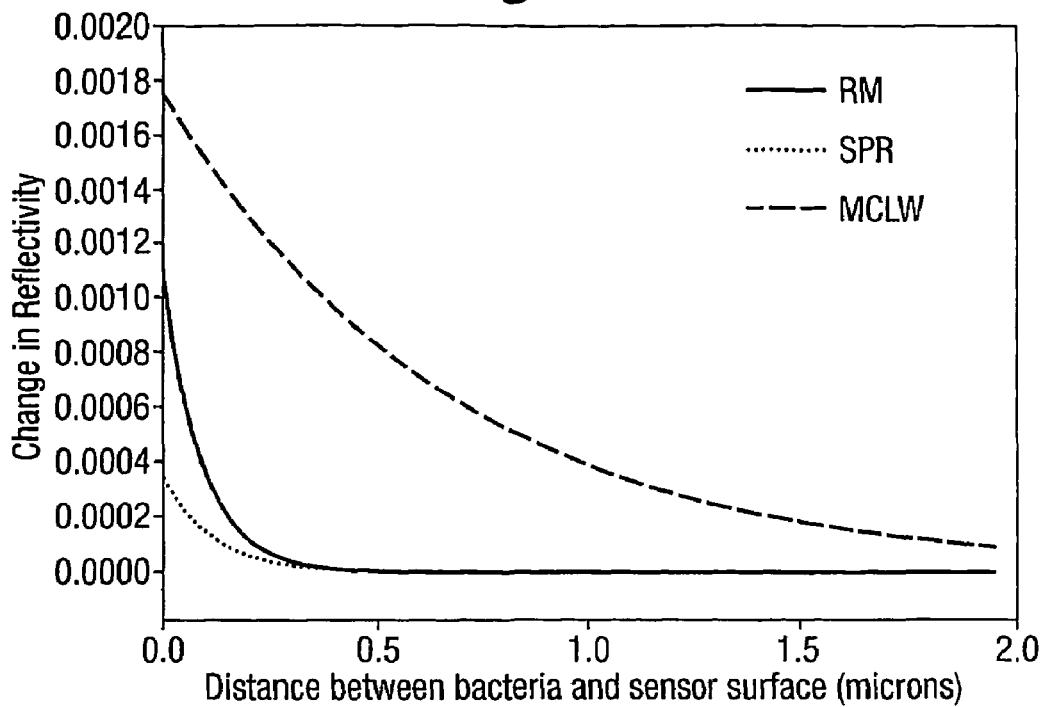

Referring now to FIG. 5, the change in reflectivity of the waveguide as a function of the distance between the upper surface of the chip 18 and the bound bacterium is compared with change in the reflectivity of commonly used SPR and resonant mirror structures. As may be seen the change in reflectivity of the waveguide structure is far greater for the MCLW structure compared to SPR and resonant mirror structures, suggesting a greater extension of the evanescent field 13 and better detection of large particles 19 such as bacteria.

Figure 6:
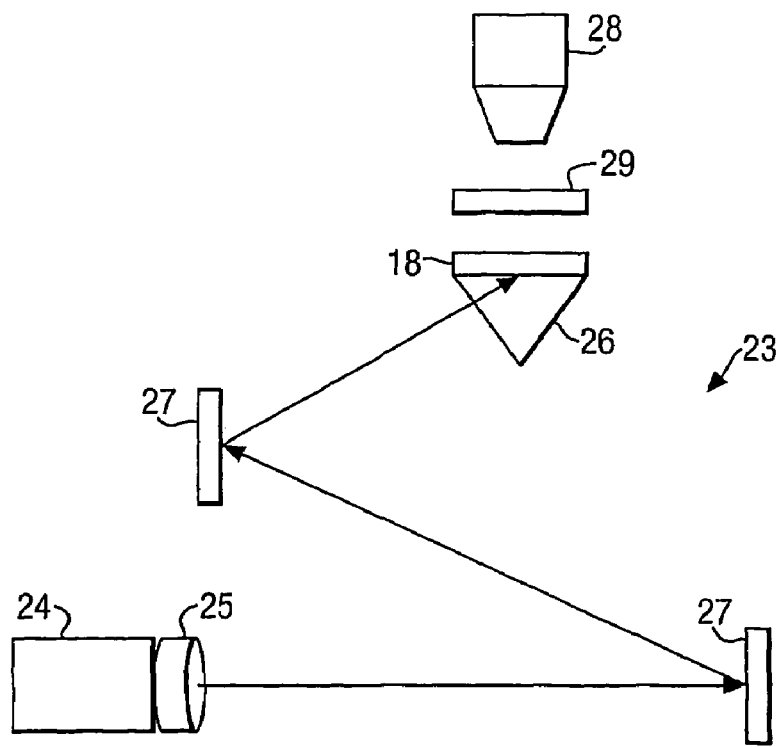

Referring now to FIG. 6, an optical sensor 23 suitable for detection of particles 19 by fluorescence comprises an air-cooled argon ion laser 24 (162LGL, Laser Graphics GmbH, Germany) with an emission wavelength of 488 μm at 10 mW power. A 488 +/−5 nm filter 25 (Glen Spectra, UK) is mounted in front of the laser to remove unwanted emissions at different wavelengths. The light is directed to a BK7 prism 26 where a proportion is coupled into the chip 18 by adjustment of mirrors 27.

The chip 18 is associated with or placed within a Perspex® flow cell (not shown) of internal diameter of about 15 mm and inlet ports diametrically opposed. A peristaltic pump (MINIPLUS-3, MP4, Canada) pumps a fluid containing particles to be analysed to the flow cell at a rate 500 μl min$^{-1}$. The pump and the chip 18 are arranged so that the direction of propagation of the leaky wave mode opposes the direction of flow of the fluid.

Light 16 emitted from the particles 17 by interaction with the evanescent field 13 is collected by a very high-resolution digital camera 28 (PULNIX™-1001, USA) comprising a 1" monochrome progressive scanning 1024 (H)×1024(V) inter-line transfer CCD imager. An emission filter 29 is provided above the chip to filter scattered light from emitted light (a 505 nm long pass filter, Comar UK) or to filter emitted light from scattered light (interference band pass filter for 488 nm, Comar, UK). The intensity of fluorescence of a particular particle 19 is calculated by summation of all pixels belonging to that particle whose value exceeds a predetermined threshold value.

Figure 1:
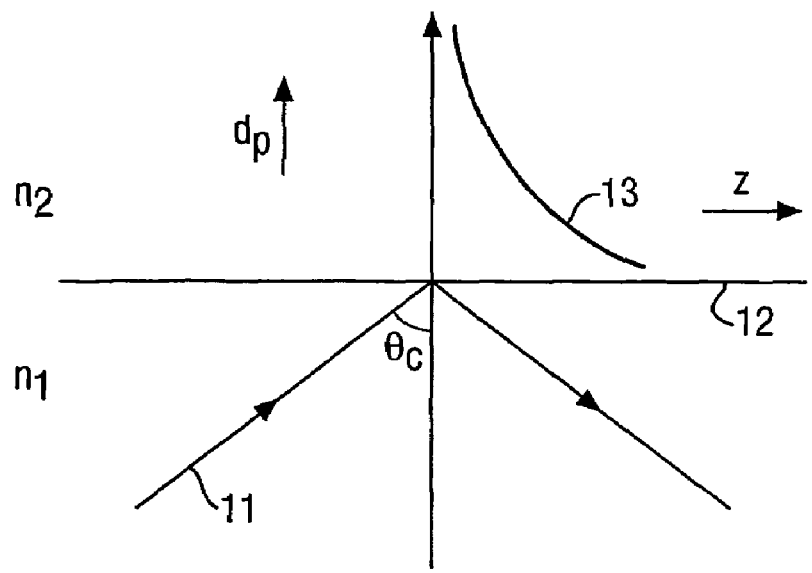
Figure 2:
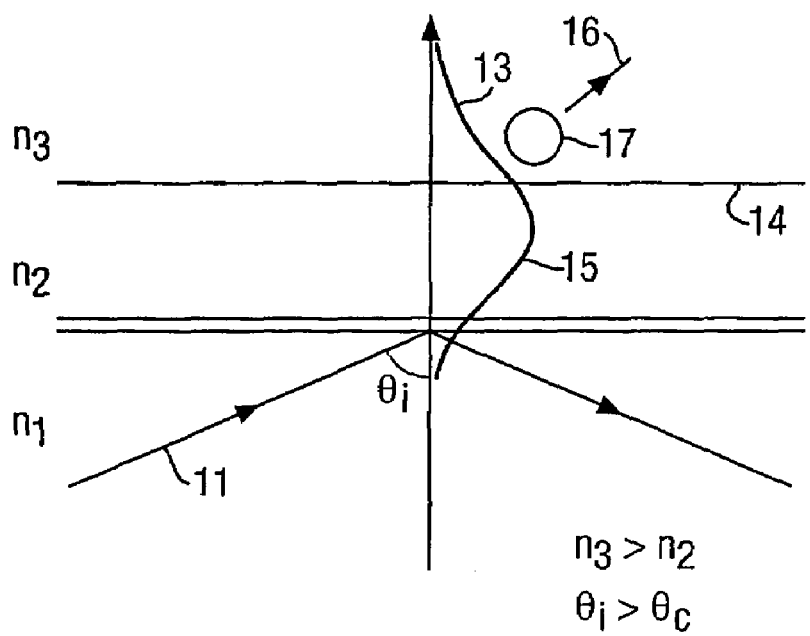
Figure 3:
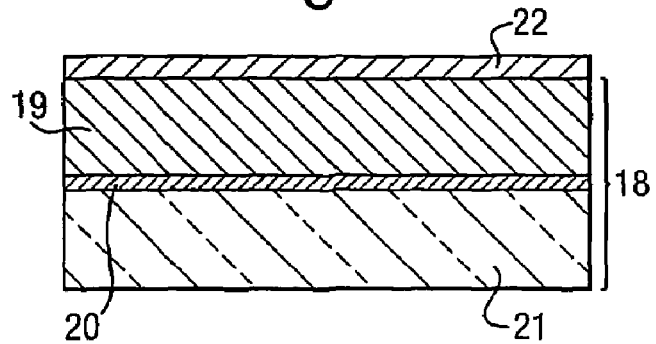

The proportion of light reflected by the chip is collected at a second detector (not shown) which can be used to monitor the reflectivity of the chip so as to maintain the incident light at the resonant angle. FIG. 7 illustrates the peak in the reflectivity of the waveguide structure of FIG. 3, which occurs at an angle of incidence of about 63°.

Figure 8A:
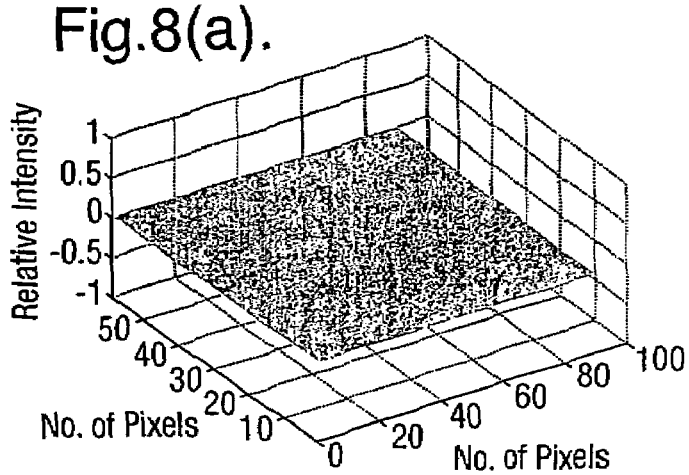

Scattering and fluorescence observations were investigated using the sensor of FIG. 6 for a number of particles, including latex beads, yeast cells, and Bacillus globiggi spores:

FIG. 8a) shows a background image of the MCLW chip. As may be seen the MCLW chip has a smooth surface with no significant imperfections such as pits or scratches that could cause scattering of light and confuse the detection of particles. The smooth surface of the MCLW chip 18 is particularly advantageous in that the necessity for a subtraction of the background image from the test image is obviated.

Figure 8B:
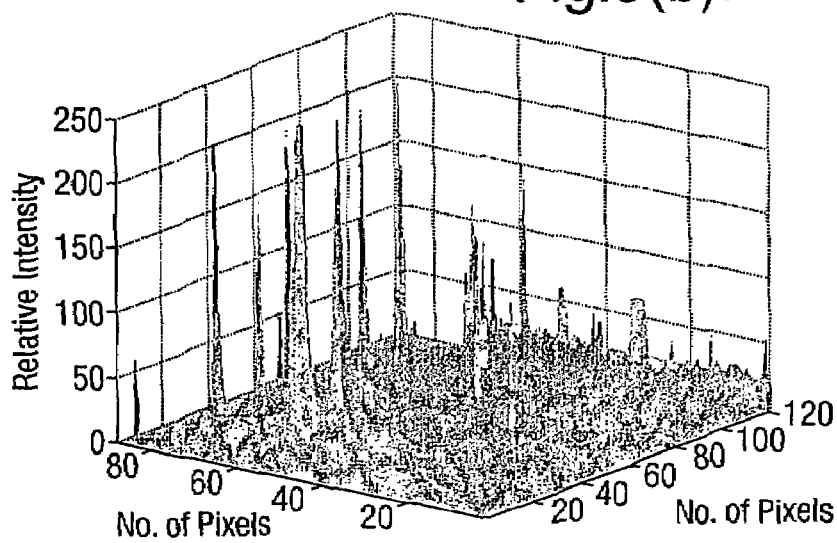

FIGS. 8b) and c) show scattering of light observed from latex beads of diameter 1.09 μm at a concentration $10^9$ beads ml$^{-1}$ in respectively full flow or a stop-start flow mode. As may be seen, the scattering of light from the beads is improved in the stop-start flow mode suggesting that the particles as settle downwards onto the sensing layer the greater their overlap of the evanescent field.

Figure 8C:
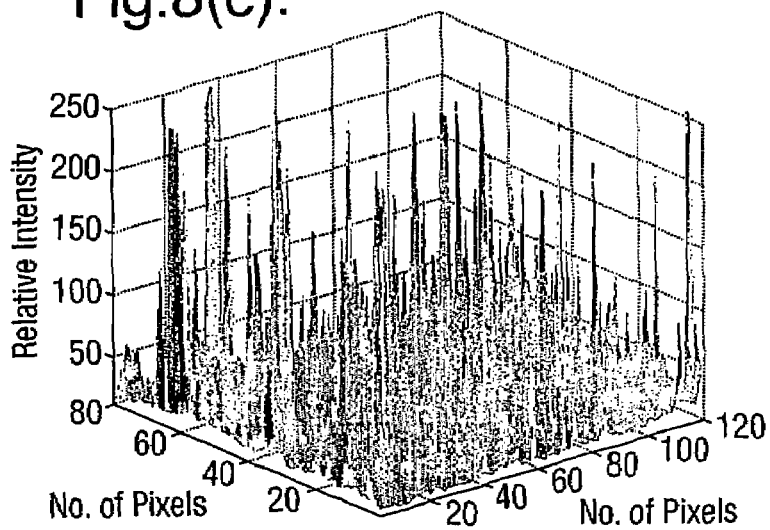
Figure 9A:
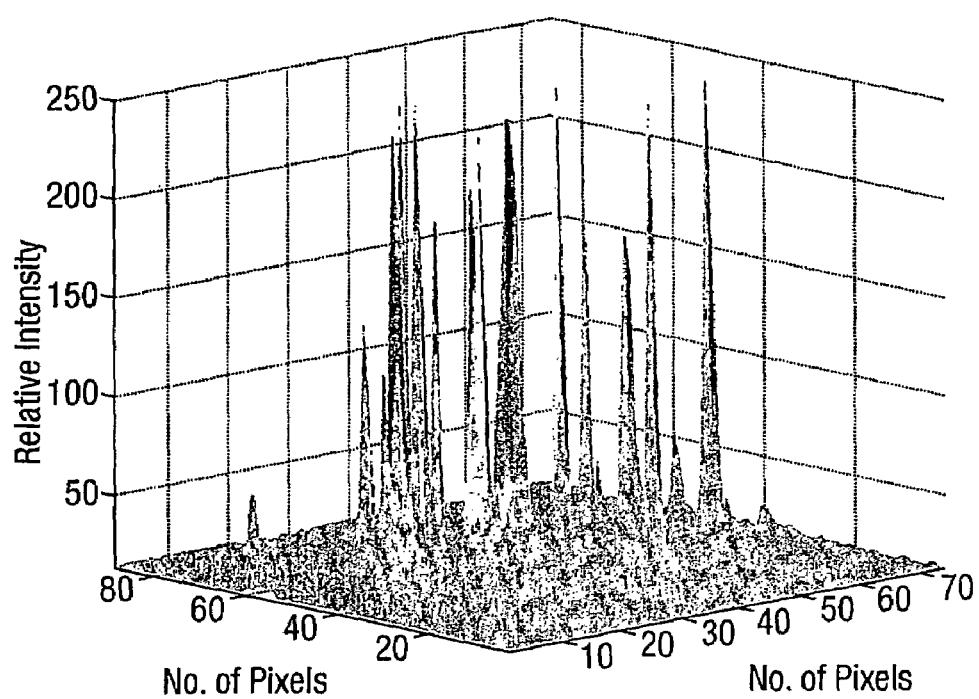
Figure 9B:
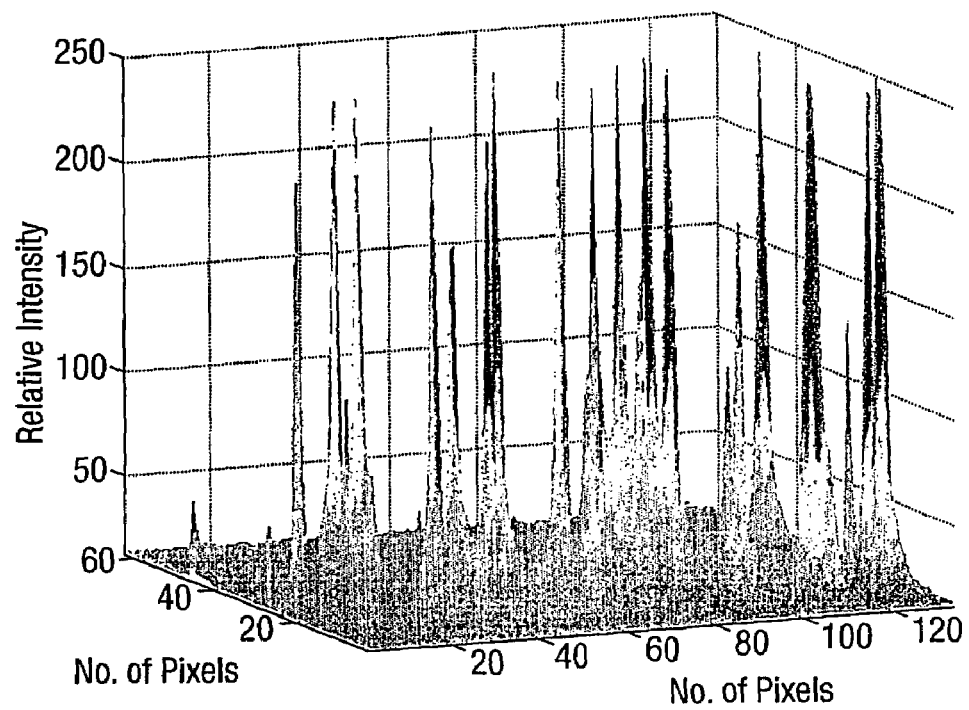

FIGS. 9a) and b) show respectively fluorescence and scattering images obtained from 100% fluorescein labelled 5 μm latex beads (Sigma, UK) at the same concentration and conditions as for FIG. 8. However, for fluorescence the laser is operated at 10 mW power and for scattering the laser is operated at 4 mW power with a simple blue filter place in front of the camera.

FIGS. 10a) to d) show images comparing scattering and fluorescence observations for 100% and 10% fluorescein labelled 2.5 μm latex beads (Sigma, UK) at 10 mW power. As may be seen from figures b) and d) the fact that the scattering images from the beads are approximately the same whilst the fluorescence images (figures a) and c)) are markedly different suggests a low level of cross talk interference between the types of images.

Figure 11A:
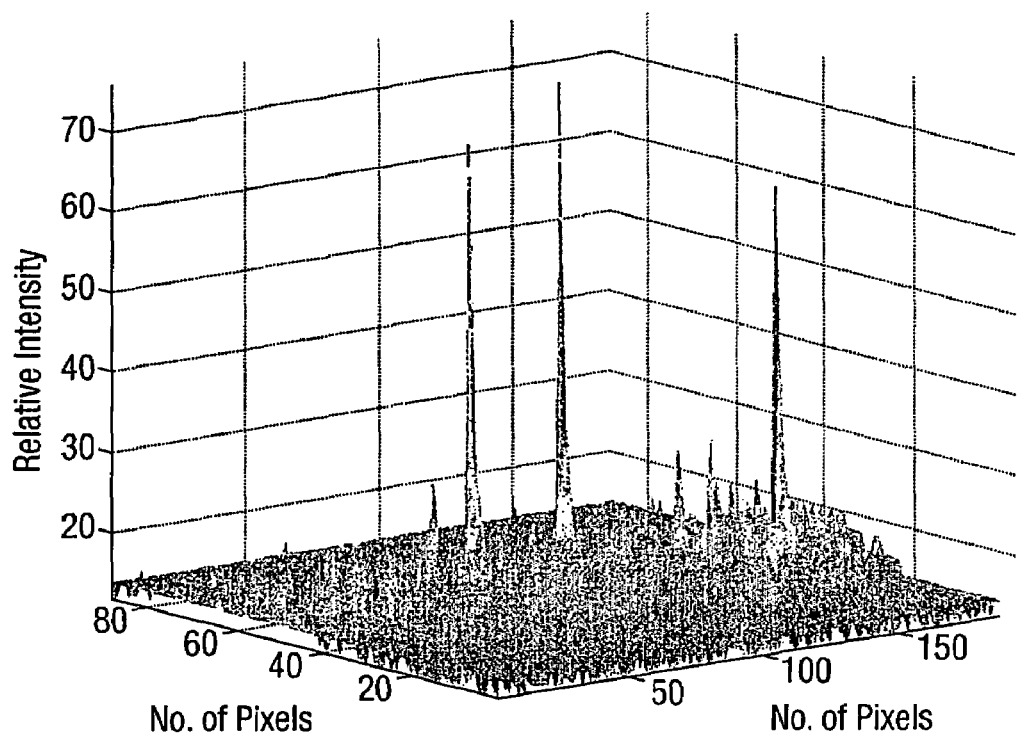
Figure 11B:
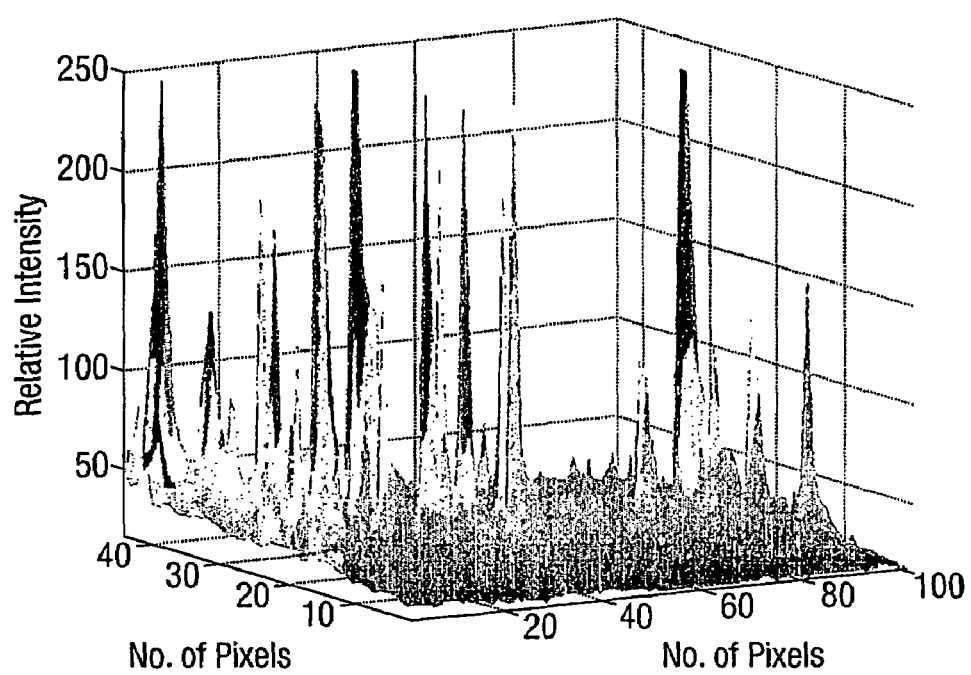

FIGS. 11a) and b) show respectively the fluorescence and scattering images from labelled yeast cells. The yeast cells, Saccharomyces cerevisiae (UMIST, UK) are genetically modified to express GFP, a green fluorescent protein obtained from Aequorea victoria, during repair of DNA damage and have a peak excitation wavelength of 490 nm and a peak emission wavelength of 517 nm. The cells were activated to express GFP by exposure to methyl methanesulphonate—a known DNA damaging compound. As may be seen the fluorescence images are inferior, even at 10 mW power, to the scattering images suggesting that the only yeast cells producing levels of GFP are detected. Further comparison of FIG. 11a) with FIG. 10a) suggests that the percentage of yeast cells expressing high levels of fluorescein is lower than 2.5%. Further the images of the yeast obtained suggest that they vary in size between 3 to 8 μm according to their stage in the cell cycle. Comparison of FIG. 11b) with FIG. 10b) clearly shows that detection of yeast cells by scattering of light is also more difficult than detection of latex beads. This may be attributable to the fact that latex beads have a higher refractive index than yeast cells and so scatter light more strongly.

Figure 12:
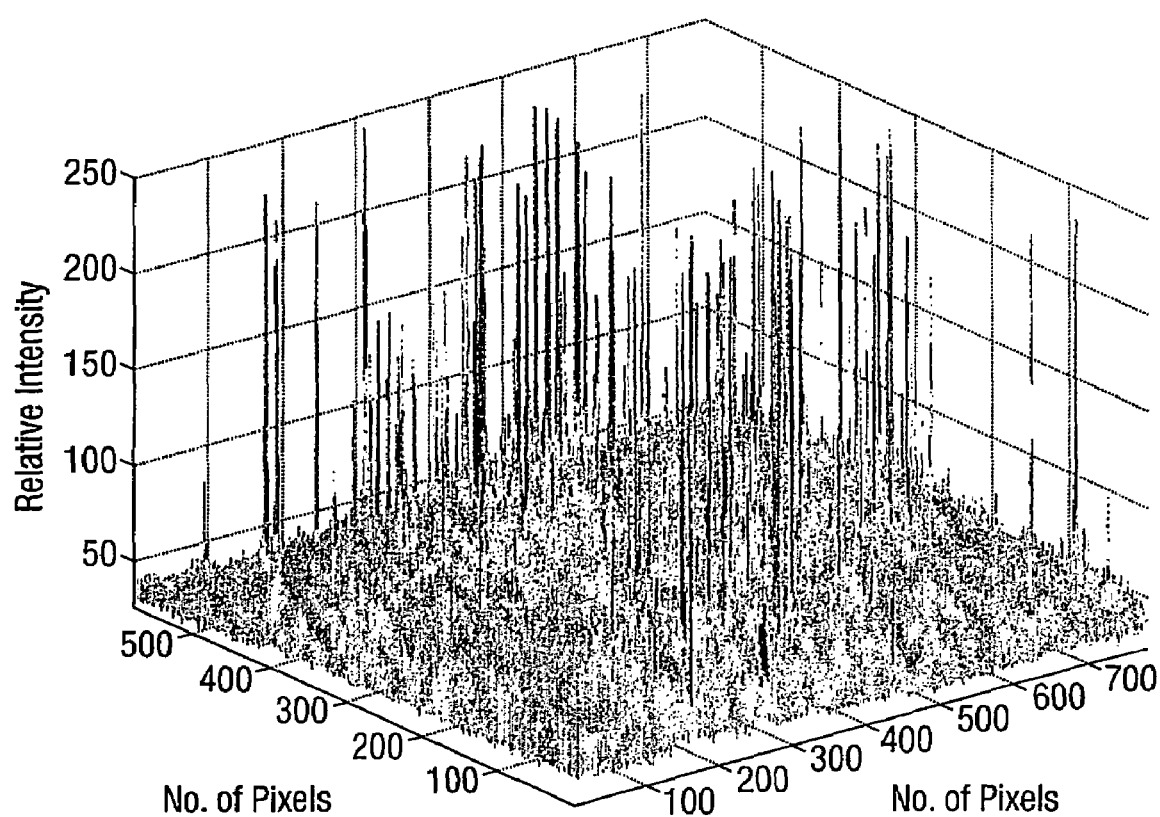

Exposure of the sensor to Bacillus globiggi spores (CAMR, UK) revealed the spores as areas of diffuse light moving across the surface of the chip. Where the spores appeared to move close to the surface of the chip they were observed on occasion to come to an instantaneous stop being presumably captured by an antibody. Such behaviour was not observed when the sensor was coated with a surface comprising BSA rather than antibody. Again the stop start flow mode appeared to allow settling of the spores onto the chip where the images became brighter and more well defined. FIG. 12 shows the scattering image obtained after exposure of the chip to Bacillus globiggi spores at a concentration of $10^7$ spores ml$^{-1}$ for 1 h. It will be realised that the response of the MCLW sensor compares favourably with SPR sensors, which generally require concentrations of *Bacillus globiggi* of $10^9$ spores per $ml^{-1}$ for adequate detection.

The scattering intensity was compared with the scattering intensity when the spores are exposed to an SPR sensor. The results are summarised in Table 1. As may be seen, the scattering intensity from the MCLW chip is about three times as strong as the scattering intensity from the SPR chip. The standard deviation in the experimental results is higher in the case of the MCLW chip since the depth of penetration of the evanescent field is higher and although the probability of overlap with the particles higher they are also detectable at larger distances from the chip surface.

TABLE 1

| Type of chip | Intensity of Scattering (before settling) | Intensity of Scattering (after settling) |
|---|---|---|
| SPR | 45 +/− 9% | 73 +/− 2% |
| MCLW | 125 +/− 15% | 192 +/− 4% |

These results show that a MCLW sensor has been developed, based on the scattering or emission of light, which is capable of detecting particles and more sensitive than other currently used sensors. The sensor increases the depth of penetration of an evanescent field from the sensor surface into the sample and the extent of propagation of the mode thus providing an effective interrogation for the detection of particles.

The invention claimed is:

1. A waveguide structure for detecting particles comprising a sensing layer of a medium disposed upon a second layer having a refractive index ranging from 1.33 to 1.45, said second layer being disposed upon a third layer of refractive index higher than that of the second layer, the structure being capable of supporting a bulk optical mode in the second layer, the medium being adapted to trap a target particle having a diameter ranging from 1 to 10 μm that results in a change in an optical property of the sensing layer and the thickness and/or refractive index of the second layer being such that when light is incident the upper surface of the third layer the optical mode generated in the second layer penetrates into the sensing layer so as to overlap at least a major portion of the particle.

2. A waveguide structure according to claim 1, further comprising a highly reflective fourth layer disposed between the second layer and the third layer.

3. A waveguide structure according to claim 1, in which the thickness of the second layer ranges from 300 nm to 500 nm.

4. A waveguide structure according to claim 1, in which the second layer comprises silica, an agarose gel, a fluorinated polymer or a polyacrylate.

5. A waveguide structure according to claim 1, in which the fourth layer comprises a metal or solid dye material.

6. A waveguide structure according to claim 5, in which the metal comprises zirconium, chromium, aluminum, tantalum or titanium.

7. An optical sensor according to claim 6, in which the particle is a bacterium.

8. An optical sensor comprising the waveguide structure of claim 1, an optical source, means for coupling light from the optical source into the optical mode and means for detecting light scattered or emitted by a particle in the sensing medium.

9. An optical sensor according to claim 8, further comprising means for detecting changes in the properties of the optical mode by monitoring properties of light coupled from the waveguide structure.

10. An optical sensor according to claim 8, in which the wavelength of light emitted by the optical source is 488 nm or 635 nm.

* * * * *